United States Patent
Rajamannar et al.

(10) Patent No.: US 7,148,364 B2
(45) Date of Patent: *Dec. 12, 2006

(54) PROCESS FOR THE PREPARATION OF 1-[3-(DIMETHYLAMINO)PROPYL]-1-(4-FLUOROPHENYL)-1,3-DIHYDRO-5-ISOBENZOFURAN CARBONITRILE

(75) Inventors: Thennati Rajamannar, Baroda (IN); Kilaru Srinivasu, Baroda (IN); Nileshkumar Sureshbhai Patel, Baroda (IN); Chinnapillai Rajendran, Hyderabad (IN)

(73) Assignee: Sun Pharmaceutical Industries, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/500,532

(22) PCT Filed: Jan. 7, 2003

(86) PCT No.: PCT/IN03/00006

§ 371 (c)(1),
(2), (4) Date: Jul. 19, 2004

(87) PCT Pub. No.: WO03/057132

PCT Pub. Date: Jul. 17, 2003

(65) Prior Publication Data

US 2005/0043550 A1    Feb. 24, 2005

(30) Foreign Application Priority Data

Jan. 7, 2002   (IN) .......................... 10/MUM/2002
Jan. 10, 2002  (IN) .......................... 18/MUM/2002
Sep. 30, 2002  (IN) ......................... 847/MUM/2002

(51) Int. Cl.
C07D 307/87    (2006.01)

(52) U.S. Cl. ...................... 549/467; 549/462; 549/465

(58) Field of Classification Search ................ 549/462, 549/467, 469, 465
See application file for complete search history.

(56) References Cited

U.S. PATENT DOCUMENTS

| 4,136,193 | A | 1/1979 | Bogeso et al. | |
|---|---|---|---|---|
| RE34,712 | E | 8/1994 | Boegesoe et al. | |
| 6,426,422 | B1 * | 7/2002 | Petersen et al. | 549/467 |
| 6,455,710 | B1 * | 9/2002 | Villa et al. | 549/462 |
| 6,509,483 | B1 * | 1/2003 | Petersen et al. | 549/467 |
| 6,635,773 | B1 * | 10/2003 | Coppi et al. | 549/467 |
| 6,781,003 | B1 * | 8/2004 | Kaushik et al. | 549/467 |
| 6,812,355 | B1 * | 11/2004 | Chodankar et al. | 549/467 |
| 6,903,228 | B1 * | 6/2005 | Hamied et al. | 549/467 |
| 6,967,259 | B1 * | 11/2005 | Malik et al. | 564/320 |
| 2001/0031784 | A1 * | 10/2001 | Petersen et al. | 514/469 |
| 2002/0077353 | A1 | 6/2002 | Petersen et al. | |
| 2003/0078442 | A1 | 4/2003 | Petersen et al. | |

FOREIGN PATENT DOCUMENTS

| GB | 2387596 A * | 10/2003 |
|---|---|---|
| WO | WO 98/19512 | 5/1998 |
| WO | WO 98/19513 | 5/1998 |
| WO | WO 99/30548 | 6/1999 |
| WO | WO 00/11926 | 3/2000 |
| WO | WO 00/23431 | 4/2000 |
| WO | WO 01/02383 | 7/2001 |
| WO | WO 01/47877 | 7/2001 |
| WO | WO 01/68627 A1 * | 9/2001 |
| WO | WO 03/029236 | 4/2003 |

* cited by examiner

*Primary Examiner*—Sabiha N. Qazi
(74) *Attorney, Agent, or Firm*—Pharmaceutical Patent Attorneys, LLC

(57) ABSTRACT

The present invention provides a process for the preparation of crude 1-[3-(dimethylamino)propyl]-1-(4-fluorophenyl)-1,3-dihydro-5-isobenzofuran carbonitrile base with substantially low levels of impurities by arresting the formation of substantial amount of carboxamide impurity, high molecular weight impurities and suppressing the formation of desmethylcitalopram besides taking the cyanide exchange reaction to near completion and thus avoiding an extensive and expensive purification process.

26 Claims, No Drawings

PROCESS FOR THE PREPARATION OF 1-[3-(DIMETHYLAMINO)PROPYL]-1-(4-FLUOROPHENYL)-1,3-DIHYDRO-5-ISOBENZOFURAN CARBONITRILE

The present invention relates to a process for preparation of 1-[3-(dimethylamino)propyl]-1-(4-fluorophenyl)-1,3-dihydro-5-isobenzofuran carbonitrile, a compound of Formula 1, commonly known as citalopram (INN name), a well known

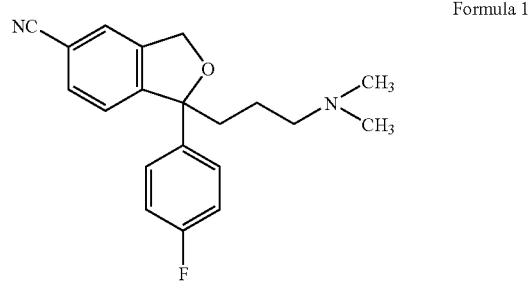

Formula 1 antidepressant. Preparation of 1-[3-(dimethylamino)propyl]-1-(4-fluorophenyl)-1,3-dihydro-5-isobenzofuran carbonitrile was first disclosed in U.S. Pat. No. 4,136,193. Subsequently several other patents appeared in the literature regarding enriching crude citalopram base or salt purity so as to obtain pharmaceutically acceptable base or acid addition salts.

U.S. Pat. No. 4,136,193 (hereinafter referred to as the '193 patent) claims 1-[3-(dimethylamino) propyl]-1-(4-fluorophenyl)-1,3-dihydro-5-isobenzofuran carbonitrile and its pharmaceutically acceptable acid addition salts. It discloses a process for the preparation of 1-[3-(dimethylamino) propyl]-1-(4-fluorophenyl)-1,3-dihydro-5-isobenzofuran carbonitrile from the penultimate 5-substituted derivatives, compounds of Formula (2) wherein R is halogen or triflates, by reaction with a cyanide source. In this process wherein the group 'R' is replaced with the cyano group is referred to as cyanide exchange process hereinafter.

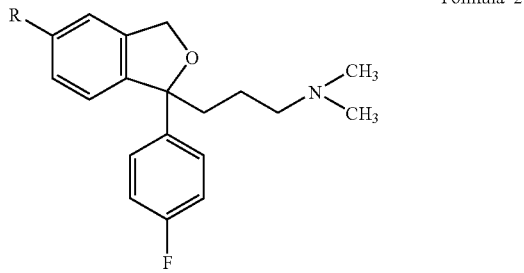

Formula 2

The cyanide exchange process as illustrated in example 2 of the '193 patent involves reaction of compound of formula (2) with cupro cyanide in dimethylformamide by refluxing for 4 hours, followed by work-up of the reaction mixture to get the crude citalopram base. In the work-up of the reaction the organic phase is washed with 10% sodium cyanide solution, treated with activated carbon, the resultant oil dissolved in ether and extracted with 20% aqueous acetic acid and the aqueous phase neutralized with NaOH solution and extracted in ether, dehydrated and treated with active carbon and vacuum evaporated to obtain citalopram crude base as an oil. It contains unreacted starting material and many other impurities.

Several other patents for newer synthetic methods have also been reported in the literature for preparing citalopram as mentioned below:
1. Conversion 5-amido or ester group to a 5-cyano group (WO 9819513)
2. Conversion 5-amino group to a 5-Cyano group (WO 9819512)
3. Conversion 5-formyl group to a 5-Cyano group (WO 9930548)
4. Conversion 5-oxazolinyl or thiazolinyl group to a 5-Cyano group (WO 0023431)
5. Conversion 5-halo group to a 5-Cyano group (WO 0011926)
6. Conversion 5-halo group to a 5-Cyano group (WO 0013648)

The PCT application WO 0147877 discloses preparation of 1-[3-(dimethylamino) propyl]-1-(4-fluorophenyl)-1,3-dihydro-5-isobenzofuran carbonitrile, by the cyanide exchange process in sulfolane solvent, instead of dimethylformamide solvent as in example 2 of the '193 patent. It is reported that the cyanide exchange process for preparation of citalopram as in the '193 patent, gives some high molecular weight impurities including dimeric reaction products in unacceptable amounts and that these impurities are difficult to remove by usual working up procedures leading to extensive and expensive purification processes. Even using sulfolane as a solvent the purity reported by HPLC is about 85%, which is further purified by film distillation process to obtain citalopram of 96% purity.

The PCT application WO 0145483 (the U.S. Pat. No. 6,455,710 is its equivalent) discloses a cyanide exchange process for preparation of 1-[3-(dimethylamino)propyl]-1-(4-fluorophenyl)-1,3-dihydro-5-isobenzofuran carbonitrile from the compounds of formula 2, wherein the group R is selected from chloro, bromo, iodo or $CF_3$—$(CF_2)_n$—$SO_2$—O—, n being from 0 to 8, by reaction with a cyanide source and subsequently treating the resultant crude citalopram with an amide or an amide-like group forming agent for removing desmethylcitalopram impurity, a compound of formula 3,

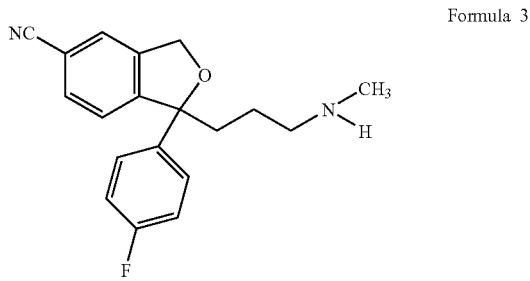

Formula 3 generated during cyanide exchange process. This PCT application teaches that desmethylcitalopram impurity is removed by reacting with a reagent that converts it into amide or an amide-like neutral derivative, which subsequently can be removed by means of acid base treatment. The reagents like acid halides, acid anhydrides have been disclosed for removal of desmethylcitalopram impurity. Acetic anhydride and acetyl chloride are the preferred reagents and use of acetic anhydride has been exemplified. These reagents transform basic secondary amine i.e. desmethylcitalopram to the neutral form, wherein the tertiary amine viz., the 1-[3-(dimethylamino)propyl]-1-(4-fluorophenyl)-1,3-dihydro-5-isobenzofuran carbonitrile remains unaltered, hence displaying the basic character, thereby making the process suitable to eliminate the desmethylcitalopram that gets transformed into a neutral derivative which can be removed by means of acid base treatment. However, this method does not remove the carboxamide impurity, a compound of formula 4, that is generated during cyanide exchange process hence the disclosure is not a complete solution to improve the efficiency of the process.

Formula 4

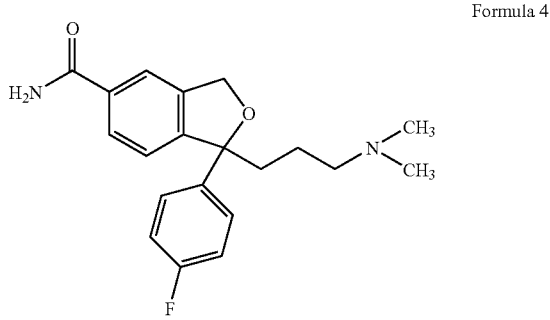

The end product obtained by the above-mentioned prior art processes is crude citalopram in an oil form. These prior art patents do not teach any method for purifying the base further to obtain crystalline base of citalopram.

In general the processes described generates many of the side products, which needs to be removed in order to make pharmaceutically acceptable product. The PCT application WO 0013648 (equivalent of United States Patent Application US 2002/0077353 A1) states that the exchange of 5-bromo group to 5-cyano is not very convenient in commercial scale, since the yield was rather low, the product was impure and in particular that it was very difficult to separate the resulting citalopram from the corresponding starting 5-bromo compound.

The reissued U.S. Pat. No. RE 34,712 describes synthesis of crystalline citalopram base in example 3, starting from a racemic diol via a methanesulfonyl ester in dichloromethane in presence of triethylamine. The reaction mixture was washed with 0.1M NaOH solution twice, the organic phase separated, dried and evaporated to obtain a crystalline citalopram base.

PCT application WO 0168627 (equivalent United States Patent Application US 2001/0031784 A1) describes a process for purification of citalopram base to obtain 99.8% w/w pure, preferably more than 99.9% w/w pure crystalline base. As can be seen from example 1 of WO 01/68627, the citalopram hydrobromide is suspended in water and toluene, neutralized by addition of NaOH, phases are separated and organic phase is washed with water and filtered. The volatiles are removed in vacuum and the obtained citalopram base that is still in an oil form is crystallized from n-heptane. In all the worked out examples the crystalline base is obtained starting from a citalopram salt. The patent teaches use of an aprotic solvent for crystallisation, such as an alkane, including n-heptane, hexane and isooctane, and high and low boiling petroleum ethers and substituted aromates, including toluene and xylenes. In all the worked out examples n-heptane has been employed.

The PCT application WO 01/02383 relates to a process for preparation of citalopram via an aldehyde intermediate. The text teaches that citalopramn obtained in the form of oil can be crystallized to obtain pure product by dissolution in isopropanol (referred herein as IPA), followed by crystallization. However, the removal of polar and non-polar impurities in a single crystallization step is not disclosed.

None of the relevant prior art methods provide a crystallization process, which in a single step yields crystalline citalopram base by simultaneous removal of polar and non-polar impurities. Also no prior art reference teaches the use of a combination of solvents for simultaneous removal of the polar and non-polar impurities in a single crystallization step.

The major impurities that are formed when 1-[3-(dimethylamino)propyl]-1-(4-fluorophenyl)-1,3-dihydro-5-isobenzofuran carbonitrile is prepared by cyanide exchange process disclosed in the '193 patent, are compounds of formulae 3 and 4. Presence of these impurities poses difficulty in purifying the crude 1-[3-(dimethylamino)propyl]-1-(4-fluorophenyl)-1,3-dihydro-5-isobenzofuran carbonitrile base to the desired quality of end product.

During the process the amide impurity, a compound of formula 4, may be formed to an extent of about 10%, and normally it ranges from about 1 to about 10% depending on the reaction conditions. The range of formation of this impurity is wide, hence developing a process which removes the impurity in one unit operation, say crystallisation or distillation or any other purification, proved to be very difficult and unpredictable. Therefore one needs to use multiple solvent crystallisation to obtain the desired product, which makes the whole process lengthy, and also use of several reactors during purification males it unworthy.

To devise a suitable process in order to improve purity, we envisaged that reaction of reagents, referred to herein as cyanide reversal agents, like oxy compounds of phosphorous with the crude citalopram base that is prepared by a cyanide exchange process, would result in the conversion of the amide impurity to cyanide i.e. the formation of 1-[3-(dimethylamino)propyl]-1-(4-fluorophenyl)-1,3-dihydro-5-isobenzofuran carbonitrile back from the amide, with concomitant elimination of desmethylcitalopram by forming a water soluble species in neutral, acidic or alkaline conditions.

Thus the process developed and described provides a viable method of getting high quality product with better yield, by reversing the amide impurity to the desired 1-[3-(dimethylamino)propyl]-1-(4-fluorophenyl)-1,3-dihydro-5-isobenzofuran carbonitrile. Concomitant removal of desmethylcitalopram impurity by forming the neutral species with the cyanide reversal agents was found to be an additional benefit. Hence this process obviates use of multiple solvents and operations making it user friendly.

We have observed that the use of hydrocarbon solvents to remove a mixture of residual impurities consisting polar and non-polar components from crude citalopram base was not efficient.

Further object of the present invention is to remove the polar and non-polar impurities using one solvent system either by using pure solvent or solvent mixture consisting of more than one solvent. Known processes for preparation of citalopram, yield citalopram that may contain both polar and non-polar impurities, for example, the cyanide exchange process as in example 2 of U.S. Pat. No. 4,136,193 yields citalopram with major impurities that include, the starting 5-bromo compound, viz., [1-(3-dimethylamino)propyl)]-1-(4-fluorophenyl)-1,3-dihydro-5-bromoisobenzofuran, a compound of formula 2 wherein R is Br; desmethylcitalopram, viz., [1-(3-Methylamino)propyl)]-1-(4-fluorophenyl)-1,3-dihydro-5-isobenzofurancarbonitrile, a compound of formula 3; an amide, viz., [1-(3-Dimethylamino)propyl)]-1-(4-fluorophenyl)-1,3-dihydro-isobenzofuran-5-carboxylic acid amide, a compound of formula 4; and descyanocitalopram, viz., [1-(3-Dimethylamino)propyl)-1-(4-fluorophenyl)-1,3-dihydroisobenzofuran, a compound of Formula 5, and high molecular weight impurities. Hereinafter the impurities of formula 2, 3, 4 and 5 will be referred to as 5-bromo, desmethylcitalopram, amide and descyanocitalopram, respectively.

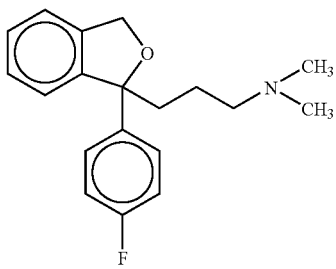

Formula 5

It has been observed that the removal of non-polar impurities like starting compound of formula 2 and descyanocitalopram, a compound of formula 5, are possible using hydrocarbon solvents, however the polar impurities like desmethylcitalopram, a compound of formula 3 and the amide, a compound of formula 4 are difficult to eliminate upon treatment with hydrocarbon solvents.

The present invention provides an improved cyanide exchange process for preparation of 1-[3-(dimethylamino) propyl]-1-(4-fluorophenyl)-1,3-dihydro-5-isobenzofuran carbonitrile.

The present invention provides a process for the preparation of 1-[3-(dimethylamino)propyl]-1-(4-fluorophenyl)-1,3-dihydro-5-isobenzofuran carbonitrile with substantially low levels of impurities from crude 1-[3-(dimethylamino) propyl]-1-(4-fluorophenyl)-1,3-dihydro-5-isobenzofuran carbonitrile by treatment with cyanide reversal agents.

The present invention provides a process for purification of 1-[3-(dimethylamino)propyl]-1-(4-fluorophenyl)-1,3-dihydro-5-isobenzofuran carbonitrile, comprising crystallizing 1-[3-(dimethylamino)propyl]-1-(4-fluorophenyl)-1,3-dihydro-5-isobenzofuran carbonitrile from a solvent system which removes both polar and non-polar impurities.

OBJECTIVES OF THE INVENTION

The objective of the present invention is to provide 1-[3-(dimethylamino)propyl]-1-(4-fluorophenyl)-1,3-dihydro-5-isobenzofuran carbonitrile of high purity by taking the cyanide exchange reaction to near completion and arrest the formation of the amide impurity, high molecular weigh impurities and to suppress the desmethylcitalopram impurity.

It is another objective of the present invention to provide 1-[3-(dimethylamino)propyl]-1-(4-fluorophenyl)-1,3-dihydro-5-isobenzofuran carbonitrile with substantially low levels of impurities, by treatment with cyanide reversal agents, and thus avoid an extensive and expensive purification process.

It is yet another objective of the present invention to provide a process for purification of 1-[3-(dimethylamino) propyl]-1-(4-fluorophenyl)-1,3-dihydro-5-isobenzofuran carbonitrile by crystallization.

SUMMARY OF THE PRESENT INVENTION

The present invention provides a process for the preparation of 1-[3-(dimethylamino)propyl]-1-(4-fluorophenyl)-1,3-dihydro-5-isobenzofuran carbonitrile base, a compound of formula 1,

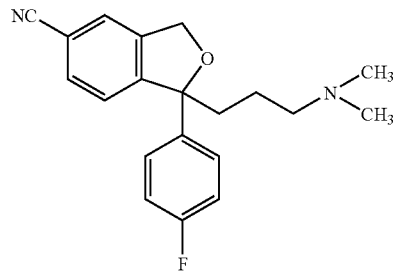

Formula 1 comprising, a) reacting a compound of formula 2, wherein R is Cl or Br,

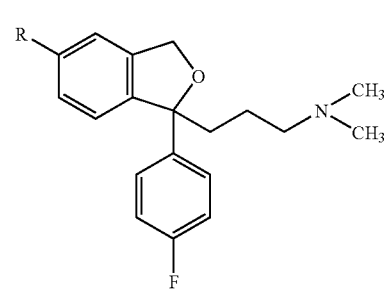

Formula 2 with a cyanide source in presence of an iodide and a suitable solvent selected from the group consisting of amides, amines and polyethers, to obtain the compound of formula 1, b) treating the resultant crude compound of formula 1 obtained in step 'a' containing the desmethylcitalopram impurity viz., 1-[3-(methylamino)propyl]-1-(4-fluorophenyl)-1,3-(dihydro-5-isobenzofuran carbonitrile, a compound of formula 3, and the amide impurity viz. 5-carboxamide-1-(3-dimethylaminopropyl)-1-(4-fluorophenyl)-phthalide, a compound of formula 4,

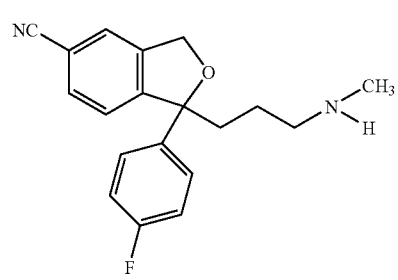

Formula 3

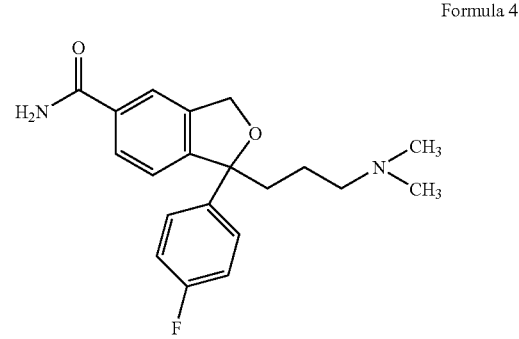

Formula 4 with a cyanide reversal agent, wherein the cyanide reversal agent is selected from phosphorous oxyhalides and phosphorous oxides; and isolating the base of compound of formula 1 from the reaction mixture, wherein the compound of formula 1 obtained after isolation has substantially low levels of impurities of formula 3 and formula 4, and optionally converting the compound of formula 1 obtained after isolation, to an acid addition salt thereof, followed by the conversion of the salt of compound of formula 1 to the base of compound of formula 1, c) further purifying the resultant compound of formula 1 obtained in step 'b', from a solvent system, wherein the solvent system comprises a first solvent which is a hydrocarbon solvent and a second solvent, wherein the second solvent is selected from a group consisting of alcohol, ester, ether, ketone or mixture thereof.

In one aspect the present invention provides a process for the preparation of 1-[3-(dimethylamino)propyl]-1-(4-fluorophenyl)-1,3-dihydro-5-isobenzofuran carbonitrile base, a compound of formula 1,

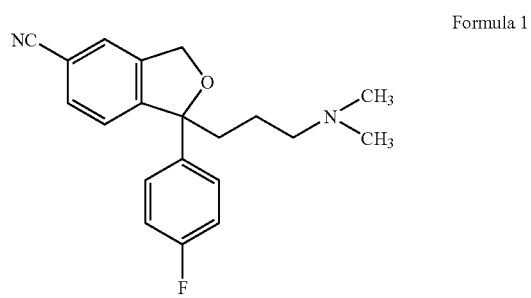

Formula 1 with substantially low levels of impurities, comprising treating the crude compound of formula 1, containing the desmethylcitalopram impurity viz., 1-[3-(methylamino)propyl]-1-(4-fluorophenyl)-1,3-(dihydro-5-isobenzofuran carbonitrile, a compound of formula 3, and the amide impurity viz. 5-carboxamide-1-(3-dimethylaminopropyl)-1-(4-fluorophenyl)-phthalide, a compound of formula 4,

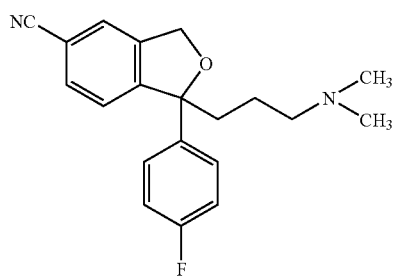

Formula 1

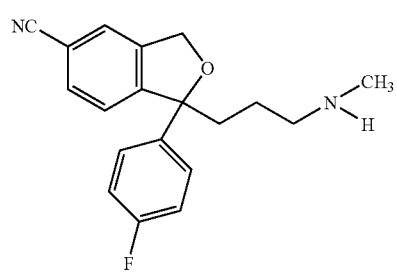

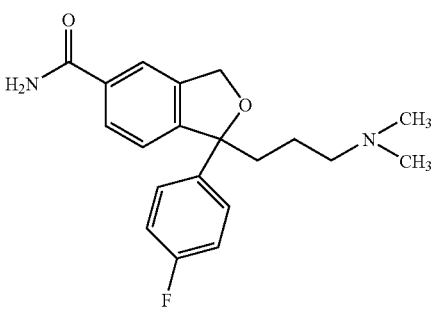

comprising reacting a compound of formula 2, wherein R is Cl or Br,

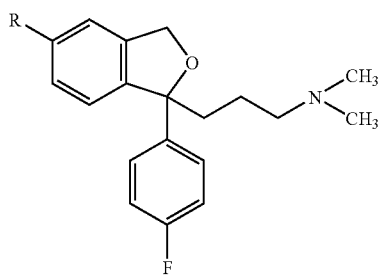

Formula 2 with a cyanide source in presence of an iodide and a suitable solvent selected from the group consisting of amides, amines and polyethers.

In another aspect the present invention provides a process for preparation of 1-[3-(dimethylamino)propyl]-1-(4-fluorophenyl)-1,3-dihydro-5-isobenzofuran carbonitrile base, a compound of formula 1, Formula 3 Formula 4 with a cyanide reversal agent, wherein the cyanide reversal agent is selected from phosphorous oxyhalides and phosphorous oxides; and isolating the base of compound of formula 1 from the reaction mixture, and optionally converting the compound of formula 1 obtained after isolation, to an acid addition salt thereof, followed by the conversion of the salt of compound of formula 1 to the base of compound of formula 1.

In yet another aspect the present invention provides a process for purification of 1-[3-(dimethylamino)propyl]-1-(4-fluorophenyl)-1,3-dihydro-5-isobenzofuran carbonitrile, a compound of formula (1), comprising

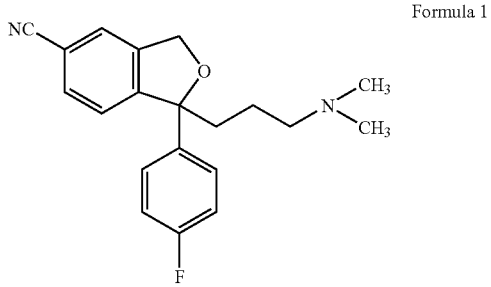

Formula 1 crystallizing the compound of formula 1 from a solvent system, wherein the solvent system comprises a first solvent which is a hydrocarbon solvent and a second solvent, wherein the second solvent is selected from a group consisting of alcohol, ester, ether, ketone or mixture thereof.

DETAILED DESCRIPTION OF THE INVENTION

According to the process of the present invention, for the reaction with a compound of formula 2, the cyanide source is selected from the group consisting of KCN, NaCN, CuCN and $[R_1R_2R_3R_4N]CN$, wherein $R_1$, $R_2$, $R_3$ and $R_4$ are the same or different groups selected from hydrogen and straight chain or branched alkyl, and the like, preferably KCN, NaCN and CuCN, the most preferred being CuCN.

According to the process of the present invention the iodides that may be used in the present invention for the reaction of compound of formula 2 with a cyanide source, are selected from stable metal iodides, alkali and alkaline earth metal iodides. The preferred iodides being alkali and alkaline earth metal iodides and the most preferred being alkali metal iodides like potassium iodide.

According to the process of the present invention the iodide may be employed in the range of about 0.1–10 molar equivalents per equivalent of starting material of formula 2, preferably in the range of about 1–5, and more preferably in the range of about 1–3.

According to the process of the present invention the reaction of compound of formula 2 with a cyanide source in presence of an iodide may be carried out in a suitable solvent selected from the group consisting of amides, amines and polyethers.

According to the process of the present invention the amide solvents may be selected from N,N-dialkyl, N-alkyl, N'-aryl, N,N-diaryl, formamides, alkylamides, arylamides and N-alkyl lactams; such as dimethyl formamide, dimethyl acetamide, N-methyl,N'-phenyl formamide, N-methyl,N'-phenyl acetamide, N-methylpyrrolidone etc, preferably amide solvents having boiling point>100° C.

According to the process of the present invention the amine solvents may be selected from aliphatic amines, cyclic amines, acyclic amines of primary, secondary and tertiary nature and aromatic amines like isoquinolines, quinolines, dialkylarylamines, pyridine and substituted pyridines. The preferred amine solvents are aliphatic, cyclic or acyclic tertiary amines, pyridine and substituted pyridine solvents such as lutidine. The most preferred being the pyridine and substituted pyridine solvents like lutidine. The substituted pyridines are symmetrical polyalkyl substituted, unsymmetrical polyalkyl substituted and dimethylamino pyridine like bases.

According to the process of the present invention the polyether solvents may be selected from polyethyleneglycols, diarylethers, alkylarylethers etc. The preferred being polyethyleneglycols and diaryl ethers and the most preferred being polyethyleneglycol (PEG) with a molecular weight between the range of 200–10,000.

The amide, amine and polyether solvents can be used as a mixture in the range of 1–99% or as neat solvents, the most preferred being as neat solvent.

In a preferred embodiment the reaction of compound of formula 2 is carried out with CuCN in presence of potassium iodide, in a solvent selected from pyridine and lutidines.

According to the process of the present invention the reaction of compound of formula 2 with a cyanide source in presence of an iodide, is carried out at a temperature between the range of about 100° C. to about 200° C. for about 10 to about 30 hours, preferably at a temperature between the range of about 120° C. to about 160° C. for about 20 to about 30 hours and more preferably at a temperature between the range of about 130° C. to about 150° C. for about 20 to about 28 hours.

To further improve the purity of the crude 1-[3-(dimethylamino)propyl]-1-(4-fluorophenyl)-1,3-dihydro-5-isobenzofuran carbonitrile, a compound of Formula 1, prepared by the cyanide exchange process of the present invention, we envisaged that reaction of reagents, referred to herein as cyanide reversal agents, like oxy compounds of phosphorous with the crude compound of formula 1, would result in the conversion of the amide impurity, a compound of formula 4, to cyanide i.e. the formation of 1-[3-(dimethylamino)propyl]-1-(4-fluorophenyl)-1,3-dihydro-5-isobenzofuran carbonitrile back from the amide impurity, with concomitant elimination of desmethylcitalopram, a compound of formula 3, by forming a water soluble species in neutral, acidic or alkaline conditions.

We found upon treating crude 1-[3-(dimethylamino)propyl]-1-(4-fluorophenyl)-1,3-dihydro-5-isobenzofuran carbonitrile base containing 1–10% of amide and 0.5–10% of desmethylcitalopram with the reagents of phosphorous oxy compounds, like phosphorous oxyhalides and phosphorous oxides, gave substantial enrichment in purity, wherein the amide impurity reduced to below 1% due to reversal of the amide to 1-[3-(dimethylamino)propyl]-1-(4-fluorophenyl)-1,3-dihydro-5-isobenzofuran carbonitrile and the desmethylcitalopram also reduced to below 1%. With phosphorous oxychloride the amide and desmethylcitalopram impurities reduced to below 0.5%.

According to the process of the present invention the cyanide reversal agent that is employed for preparation of compound of formula 1, with substantially low levels of impurities from crude compound of formula 1, is selected from phosphorous compounds such as phosphorous oxyhalides and phosphorous oxides. The halides that can be used are chlorides and bromides, preferred being chlorides. The preferred cyanide reversal agent is being selected from phosphorous compounds wherein phosphorous is with valency [III] or [V], e.g. phosphorous trichloride ($PCl_3$), phosphorous oxychloride ($POCl_3$), phosphorous pentoxide ($P_2O_5$). The particularly preferred cyanide reversal agent is selected from phosphorous oxyhalides such as phosphorous oxychloride and phosphorous oxides such as phosphorous pentoxide. The most preferred cyanide reversal agent being phosphorous oxychloride.

The term cyanide reversal agent, as used herein refers to the fact that these agents are capable of, i) reacting with the amide impurity of formula 4, and convert it to the citalopram i.e. the amide group in the amide impurity is converted to cyanide group, resulting into formation of citalopram; and ii) converting the desmethylcitalopram impurity of formula 3, in to a water soluble species in neutral, acidic or alkaline conditions, that can be conveniently removed during work-up, resulting into citalopram having substantially low levels of impurities.

In a preferred embodiment the process of the present invention results in a compound of formula 1 that contains less than about 1% desmethylcitalopram, a compound of formula 3 and less than about 1% of the amide, a compound of formula 4, after treatment of compound of formula 1 with a cyanide reversal agent, followed by its isolation from the reaction mixture.

In another preferred embodiment the process of the present invention results in a compound of formula 1 that contains less than about 0.5% desmethylcitalopram, a compound of formula 3 and less than about 0.5% amide, a compound of formula 4, after treatment of compound of formula 1 with a cyanide reversal agent, followed by its isolation from the reaction mixture wherein the cyanide reversal agent is phosphorous oxychloride.

According to the process of the present invention, the ratio of the cyanide reversal agent to the crude 1-[3-(dimethylamino) propyl]-1-(4-fluorophenyl)-1,3-dihydro-5-isobenzofuran carbonitrile is in the range from about 0.1 to about 5, the preferred range being about 0.1 to about 2 and the most preferred range being about 0.2 to about 2.

Preferably, the solvent used for the reaction of crude compound of formula 1, with a cyanide reversal agent, is an aprotic organic solvent. The aprotic organic solvent may be polar or non-polar. The solvent may be selected from ethers such as tetrahydrofuran (THF), dioxane and the like; halogenated solvents such as dichloroethane, dichloromethane, chlorobenzene, dichlorobenzene and the like; aliphatic hydrocarbons such as hexane, cyclohexane and the like; aromatic hydrocarbons such as toluene, xylenes and the like; esters such as methyl acetate, ethyl acetate, benzyl acetate and the like; nitirles like acetonitrile, benzonitrile and the like; and nitro compounds such as nitromethane and nitrobenzene. The preferred solvents being ethers, aliphatic hydrocarbons, aromatic hydrocarbons, halogenated solvents, esters and nitrites and the most preferred being aliphatic and aromatic hydrocarbons, ester and nitrile solvents. In particular, aromatic hydrocarbons such as toluene or xylenes are preferred.

According to the process of the present invention, the reaction of crude compound of formula 1 with a cyanide reversal agent, can be performed at a temperature between the range of ambient to about 200° C. for about 1 to about 20 hours, preferably at a temperature between the range of about 50° C. to about 200° C. for about 1 to about 15 hours, and most preferably at a temperature between the range of about 50° C. to about 150° C. for about 1 to about 5 hours.

After treatment with the cyanide reversal agent 1-[3-(dimethylamino)propyl]-1-(4-fluorophenyl)-1,3-dihydro-5-isobenzofuran carbonitrile may be isolated by adding water to the reaction mixture; then adding an acid until the mixture is acidic, for e.g. until pH is between the range of about 1 to 4, preferably between about 1 to 3 and most preferably between about 2 to 3; and separating the aqueous phase containing 1-[3-(dimethylamino)propyl]-1-(4-fluorophenyl)-1,3-dihydro-5-isobenzofuran carbonitrile; discarding the organic phase containing the neutral species like phosphorous amides that are formed during reaction of desmethylcitalopram with the reagents like phosphorous oxychloride; and then making the aqueous phase basic by addition of a base, and extracting the mixture in an organic solvent and collecting the organic phase to obtain 1-[3-(dimethylamino)propyl]-1-(4-fluorophenyl)-1,3-dihydro-5-isobenzofuran carbonitrile. Alternately, the pH of the reaction mixture can be directly adjusted to about 9–9.5 by addition of a suitable base, followed by extraction with an organic solvent and collecting the organic phase to obtain 1-[3-(dimethylamino)propyl]-4-(4-fluorophenyl)-1,3-dihydro-5-isobenzofuran carbonitrile. The acid used may be any mineral acid, for example HCl, HBr or $H_2SO_4$ or an organic acid, and the base used may be any convenient base such as ammonia or NaOH.

The compound of formula 1 obtained after treatment with a cyanide reversal agent, followed by its isolation from the reaction mixture, can be optionally converted into an acid addition salt of the compound of formula 1, followed by its conversion into the base of the compound of formula 1. The acid addition salt may be for example, hydrobromide, hydrochloride, oxalate, sulphate etc.

In order to develop a purification method to eliminate both nonpolar and polar impurities we have investigated the use of various solvents like aliphatic linear, branched and cyclic and aromatic hydrocarbons or solvents like esters, nitriles, ethers, ketones and alcohol and found that the method is not satisfactory either in terms of overall purity or yield. But the use of a solvent system comprising of a first solvent, which is a hydrocarbon solvent in combination with a second solvent such as alcohols, esters, ethers, ketones was found to be advantageous.

According to the process of the present invention, purification of 1-[3-(dimethylamino)propyl]-1-(4-fluorophenyl)-1,3-dihydro-5-isobenzofuran carbonitrile, a compound of formula 1, may be carried out by crystallizing 1-[3-(dimethylamino)propyl]-1-(4-fluorophenyl)-1,3-dihydro-5-isobenzofuran carbonitrile from a solvent system, wherein the solvent system comprises a first solvent which is a hydrocarbon solvent and a second solvent, wherein the second solvent is selected from a group consisting of alcohol, ester, ether, ketone or mixture thereof.

Table I gives the % reduction in impurities, viz., starting 5-bromo, a compound of formula 2; desmethylcitalopram, a compound of formula 3; the amide, a compound of formula 4 and descyanocitalopram, a compound of formula 5, when 1-[3-(dimethylamino)propyl]-1-(4-fluorophenyl)-1,3-dihydro-5-isobenzofuran carbonitrile base is purified according to the process of the present invention comprising crystallization of the citalopram base from the solvent system comprising, a first solvent which is a hydrocarbon solvent and a second solvent, wherein the second solvent is selected from a group consisting of alcohol, ester, ether, ketone or mixture thereof. In the purification process of the present invention, the use of a solvent system comprising a first solvent, which is a hydrocarbon solvent in combination with a second solvent selected from esters, ethers and ketones afforded the selective removal of nonpolar impurities viz., the 5-bromo compound and descyanocitalopram effectively and the use of hydrocarbon solvents with alcohols as second solvent eliminated both non-polar and polar impurities viz., the 5-bromo compound, descyanocitalopram, desmethylcitalopram and the amide impurities to the desired level.

The process of the present invention for purification of 1-[3-(dimethylamino)propyl]-1-(4-fluorophenyl)-1,3-dihydro-5-isobenzofuran carbonitrile, a compound of formula 1, may be carried out by heating the compound of formula (1), that is to be purified in a solvent system comprising a first solvent which is a hydrocarbon solvent and a second solvent, wherein the second solvent is selected from a group consisting of alcohol, ester, ether, ketone or mixture thereof, followed by cooling to allow for crystallization of citalopram base.

The compound of formula (1), which is to be subjected to purification may be the base obtained from a crude salt of citalopram or from a crude mixture comprising the base of citalopram. The crude salt may be any convenient salt such as the hydrobromide, hydrochloride, sulphate, oxalate, phosphate, nitrate or any other convenient salts.

The terms crude salt and crude mixture refers to the fact that the salt and the mixture, respectively, comprise impurities, which must be removed. The crude salt or base may be a salt or base separated directly from the reaction mixture, or it may have been subjected to some initial purification, e.g. recrystallization, treatment with activated carbon or silica gel. The salt or the base may be prepared by any of the above-mentioned prior art processes. The salt might be obtained directly by the reaction or it may be formed subsequently by reaction of citalopram base with an acid.

The hydrocarbon solvents as the first solvents that can be employed are linear, branched, cyclic aliphatic and aromatic hydrocarbons. Examples of hydrocarbon solvents include pentane, hexane, heptane, 3-methyl hexane, 3-methyl heptane, isooctane, cyclohexane, cycloheptane, methylcyclohexane. The preferred being cyclic aliphatic hydrocarbons of 5 to 12 carbon atoms, more preferably 5 to 7 carbon atoms such as cyclohexane and cycloheptane and the most preferred being cyclohexane.

Examples of aromatic hydrocarbon solvents that can be used include benzene, toluene, xylenes, preferred being toluene and xylenes, most preferred being toluene.

The second solvent may be selected from the group consisting of alcohols, esters, ketones, ethers or mixtures thereof.

In the case of alcohol as the second solvent, linear, branched and cyclic alcohols having 1 to 10 carbon atoms, which are of primary, secondary and tertiary in nature can be employed. Examples of alcoholic solvents include methanol, ethanol, n-propanol, n-butanol, isopropanol, isobutanol, sec-butanol, t-butanol, cyclopentanol, cyclohexanol, benzyl alcohol. The preferred being alcohols of primary and secondary in nature having 1 to 5 carbon atoms such as methanol, ethanol, n-propanol, n-butanol, isopropanol, isobutanol; more preferred being n-propanol, n-butanol and isopropanol and most preferred being n-propanol and isopropanol.

In a preferred embodiment, the first solvent is cyclohexane and the second solvent is n-propanol or isopropanol.

The second solvents like esters, ketones and ethers are preferably solvents having 1 to 5 carbon atoms.

Examples of esters include methyl acetate, ethyl acetate, isopropyl acetate, butyl acetate, isobutyl acetate, sec-butyl acetate, tertiary butyl acetate, preferred being ethyl acetate, isopropyl acetate, butyl acetate and most preferred being ethyl acetate.

In a preferred embodiment, the first solvent is cyclohexane and the second solvent is ethyl acetate.

Examples of ketones include acetone, ethylmethyl ketone, methylisobutyl ketone, cyclohexyl methyl ketone, preferred being acetone, ethylmethyl ketone and most preferred is acetone.

In a preferred embodiment, the first solvent is cyclohexane and the second solvent is acetone.

Examples of ethers include diethylether, diisopropylether, tertiary butylmethylether, preferred being diethylether, tertiary butylmethylether and most preferred is diethylether.

In a preferred embodiment, the first solvent is cyclohexane and the second solvent is diethylether.

The solvent system used for purification of compound of formula 1 comprises a solvent system wherein the % solvent ratio of the first solvent to the second solvent is preferably between the range of 99:1 to 60:40, more preferably between the range of 99:1 to 75:25 and most preferably between the range of 98:2 to 80:20.

The purification of 1-[3-(dimethylamino)propyl]-1-(4-fluorophenyl)-1,3-dihydro-5-isobenzofuran carbonitrile, a compound of formula 1, may be carried out by crystallizing it from a solvent system, by heating at a temperature between the range of about about 40° C. to about 150° C., preferably about 40° C. to about 100° C., more preferably about 50° C. to about 80° C. and most preferably about 60° C. to about 80° C.

In a preferred embodiment of the present invention the solvent system employed for purification of the compound of formula 1, comprises cyclohexane:n-propanol in a % solvent ratio of 90:10, respectively.

In another preferred embodiment of the present invention the solvent system employed for purification of the compound of formula 1, comprises cyclohexane:isopropanol in a % solvent ratio of 90:10, respectively.

According to a preferred embodiment of the process of present invention, the compound of formula 1 is prepared by a process wherein, a) a compound of formula 2, wherein R is Br, is reacted with CuCN in presence of potassium iodide, in pyridine solvent to obtain the compound of formula 1, b) the resultant crude compound of formula 1 obtained in step 'a' is treated with $POCl_3$ and the compound of formula 1 is isolated from the reaction mixture, c) the resultant compound of formula 1 obtained in step 'b' is purified from a solvent system comprising cyclohexane as the first solvent and n-propanol or isopropanol as the second solvent.

The citalopram base of HPLC (High Performance Liquid Chromatography) purity greater than 99% may be obtained by the process of the present invention. The base of citalopram obtained by the process of the present invention may be further converted to a pharmaceutically acceptable acid addition salt, preferably the hydrobromide salt. The citalopram hydrobromide of HPLC purity greater than 99.5% may be obtained by converting the citalopram base obtained by the process of the present invention to the hydrobromide salt in a conventional manner.

The following examples are given by way of illustration only and not to be construed as limiting.

EXAMPLES

Comparative Example (i)

This example illustrates the preparation of 1-[3-(dimethylamino) propyl]-1-(4-fluorophenyl)-1,3-dihydro-5-isobenzofuran carbonitrile according to the prior art (U.S. Pat. No. 4,136,193).

[1-(3-dimethylamino)propyl]-1-(4-fluorophenyl)-1,3-dihydro-5-bromoisobenzofuran (50.0 g) and Copper(I) cyanide (13.0 g) in 36 ml of dimethylformamide was refluxed and worked up to obtain the crude 1-[3-(dimethylamino) propyl]-1-(4-fluorophenyl)-1,3-dihydro-5-isobenzofuran carbonitrile base with the HPLC profile as given in Table II and III.

Comparative Example (ii)

This example illustrates the preparation of 1-[3-(dimethylamino) propyl]-1-(4 fluorophenyl)-1,3-dihydro-5-isobenzofuran carbonitrile according to the prior art (U.S. Pat. No. 4,136,193)

[1-(3-dimethylamino)propyl)]-1-(4-fluorophenyl)-1,3-dihydro-5-bromoisobenzofuran (25.0 g) and Copper(I) cyanide (6.5 g) in 18 ml of dimethylformamide was refluxed and worked up to obtain the crude 1-[3-(dimethylamino) propyl]-1-(4-fluorophenyl)-1,3-dihydro-5-isobenzofuran carbonitrile base with the HPLC profile as given in Table II and Table III.

Table II and Table III show the HPLC profile of the impurities including the unreacted starting material when 1-[3-(dimethylamino) propyl]-1-(4-fluorophenyl)-1,3-dihydro-5-isobenzofuran carbonitrile was prepared according to prior art process, even when the reaction was continued for longer time the purity of the product did not improve further.

Examples 1 to 21 given below illustrate the process of the present invention.

Example 1

Potassium iodide (10 g), Copper (I) cyanide (48.5 g) were added to a solution of the [1-(3-dimethylamino)propyl)]-1-(4-fluorophenyl)-1,3-dihydro-5-bromoisobenzofuran (10 g) in pyridine (10 ml). The reaction mixture was heated to 135–145° C. and maintained for 28 hours. The reaction mixture was cooled to 100° C. and poured in ammonia solution containing toluene stirred for 2 hours to get a clear separation of layers. Then the organic layer after acid base treatment was separated and washed with water twice (2×300 ml) and dried with anhydrous sodium sulfate. The toluene layer was distilled to get the crude 1-[3-(dimethylamino) propyl]-1-(4-fluorophenyl)-1,3-dihydro-5-isobenzofuran carbonitrile base 74 gm with the following HPLC profile.

The starting 5-bromo compound 0.79%, desmethylcitalopram impurity 0.15%, the amide impurity 0.6%, higher retention time impurities <0.1% and 1-[3-(dimethylamino) propyl]-1-(4-fluorophenyl)-1,3-dihydro-5-isobenzofuran carbonitrile 94.4%.

Example 2

Potassium iodide (45 g), Copper (I) cyanide (21 g) were added to a solution of the [1-(3-dimethylamino)propyl)]-1-(4-fluorophenyl)-1,3-dihydro-5-bromoisobenzofuran (45 g) in pyridine (45 ml) and PEG-400 (45 ml). The reaction mixture was heated to 135–145° C. and maintained for 27 hours. The reaction mixture was cooled to 100° C. poured in to ammonia solution containing toluene and stirred for 2 hours to get a clear separation of layers. Then the organic layer after acid base treatment was separated and washed with water twice (2×100 ml), dried with anhydrous sodium sulfate. The toluene layer was distilled to get the crude 1-[3-(dimethylamino) propyl]-1-(4-fluorophenyl)-1,3-dihydro-5-isobenzofuran carbonitrile base 35.5 gm with the following HPLC profile.

The starting 5-bromo compound 1.01%, desmethylcitalopram impurity 0.18%, the amide impurity 0.47%, higher retention time impurities <0.1% and 1-[3-(dimethylamino) propyl]-1-(4-fluorophenyl)-1,3-dihydro-5-isobenzofuran carbonitrile 92.3%.

Example 3

Potassium iodide (25 g), Copper (I) cyanide (9.7 g) were added to a solution of the [1-(3-dimethylamino)propyl)]-1-(4-fluorophenyl)-1,3-dihydro-5-bromoisobenzofuran (25 g) in 2,6-lutidine(25 ml) and dimethylformamide (25 ml). The reaction mixture was heated to 135–145° C. and maintained for 24 hours. The reaction mixture was cooled to 100° C. and poured in to ammonia solution containing toluene stirred for 2 hours to get a clear separation of layers. Then the organic layer after acid base treatment was separated and washed with water twice (2×100 ml), dried with anhydrous sodium sulfate and finally the toluene layer was distilled to get the crude 1-[3-(dimethylamino) propyl]-1-(4-fluorophenyl)-1,3-dihydro-5-isobenzofuran carbonitrile base 17.5 gm with the following HPLC profile.

The starting 5-bromo compound 4.39%, desmethylcitalopram impurity 0.2%, the amide impurity 0.45%, higher retention time impurities <0.1% and 1-[3-(dimethylamino) propyl]-1-(4-fluorophenyl)-1,3-dihydro-5-isobenzofuran carbonitrile 93.0%.

Example 4

Potassium iodide (25 g), Copper (I) cyanide (11.8 g,) were added to a solution of the [1-(3-dimethylamino)propyl)]-1-(4-fluorophenyl)-1,3-dihydro-5-bromoisobenzofuran (25 g) in PEG-400 (25 ml). The reaction mixture was heated to 135–145° C. and maintained for 28 hours. The reaction mixture was cooled to 100° C. and poured in ammonia solution containing toluene stirred for 2 hours to get a clear separation of layers. Then the organic layer after acid base treatment was separated and washed with water twice (2×100 ml) and dried with anhydrous sodium sulfate. The toluene layer was distilled to get the crude 1-[3-(dimethylamino) propyl]-1-(4-fluorophenyl)-1,3-dihydro-S-isobenzofuran carbonitrile base 18 gm with the following HPLC profile.

The starting 5-bromo compound 4.9%, desmethylcitalopram impurity 0.54%, the amide impurity 2.74%, higher retention time impurities not observed and 1-[3-(dimethylamino) propyl]-1-(4-fluorophenyl)-1,3-dihydro-5-isobenzofuran carbonitrile 85.1%.

Example 5

Potassium iodide (25 g), Copper (I) cyanide (11.8 g) were added to a solution of the [1-(3-dimethylamino)propyl)]-1-(4-fluorophenyl)-1,3-dihydro-5-bromoisobenzofuran (25 g) in dimethylformamide (25 ml). The reaction mixture was heated to 135–145° C. and maintained for 28 hours. The reaction mixture was cooled to 100° C. and poured in ammonia solution containing toluene and stirred for 2 hours to get a clear separation of layers. Then the organic layer after acid base treatment was separated and washed with water twice (2×100 ml), dried with anhydrous sodium sulfate and finally the toluene layer was distilled to get the crude 1-[3-(dimethylamino) propyl]-14-fluorophenyl)-1,3-dihydro-5-isobenzofuran carbonitrile base 16.5 g, with the following HPLC profile.

The starting 5-bromo compound 1.91%, desmethylcitalopram impurity 0.36%, the amide impurity 8.4%, higher retention time impurities <0.1% and 1-[3-(dimethylamino) propyl]-1-(4-fluorophenyl)-1,3-dihydro-5-isobenzofuran carbonitrile 80.4%.

Example 6

A mixture of 1-[3-(dimethylamino)propyl]-1-(4-fluorophenyl)-1,3-dihydro-5-isobenzofuran carbonitrile (10.0 g, 0.03 mol) (containing 4.7% amide and 0.72% desmethylcitalopram impurities) and phosphorous oxychloride ($POCl_3$) (2 ml, 0.02 mol) in toluene (100 ml) was stirred at 70° C. under nitrogen atmosphere for 1 hour, poured into water (200 ml) and adjusted the pH to 2.0–2.5 with aqueous HCl separated the toluene layer. The pH of the aqueous layer was adjusted to 9.0–9.5 with aqueous ammonia and extracted with toluene (2×100 ml), dried over sodium sulfate, filtered and concentrated under reduced pressure. The residue was checked for HPLC purity and found 0.05% and 0.23% of the amide and desmethylcitalopram respectively.

Example 7

A mixture of 1-[3-(dimethylamino)propyl]-1-(4-fluorophenyl)-1,3-dihydro-5-isobenzofuran carbonitrile (10.0 g, 0.03 mol) (containing 5.85% amide and 7.43% desmethylcitalopram impurities) and phosphorous oxychloride ($POCl_3$) (2 ml, 0.02 mol) in toluene (100 ml) was stirred at 70° C. under nitrogen atmosphere for 1 hour, poured into water (200 ml) and adjusted the pH to 2.0–2.5 with aqueous HCl separated the toluene layer. The pH of the aqueous layer was adjusted to 9.0–9.5 with aqueous ammonia and extracted with toluene (2×100 ml), dried over sodium sulfate, filtered and concentrated under reduced pressure. The residue checked for HPLC purity and found 0.36% and 0.45% of the amide and desmethylcitalopram respectively.

Example 8

A mixture of crude 1-[3-(dimethylamino)propyl]-1-(4-fluorophenyl)-1,3-dihydro-5-isobenzofuran carbonitrile (10.0 g, 0.03 mol) (containing 8.27% amide and 0.33% desmethylcitalopram impurities) and phosphorous oxychloride ($POCl_3$) (2 ml, 0.02 mol) in toluene (100 ml) was stirred at 70° C. under nitrogen atmosphere for 1 hour, poured into water (200 ml) and adjusted the pH to 2.0–2.5 with aqueous HCl separated the toluene layer. The pH of the aqueous layer was adjusted to 9.0–9.5 with aqueous ammonia and extracted with toluene (2×100 ml), dried over sodium sulfate, filtered and concentrated under reduced pressure. The residue checked for HPLC purity and found 0.07% and 0.12% of amide and desmethylcitalopram respectively.

In the above examples 6, 7 or 8 the workup can alternately be done by adding chilled water to the reaction mixture and adjusting the pH to 9.0–9.5 with aqueous ammonia and extracting with toluene (2×100 ml), followed by the usual work-up to obtain citalopram.

Example 9

A mixture of crude 1-[3-(dimethylamino)propyl]-1-(4 fluorophenyl)-1,3-dihydro-5-isobenzofuran carbonitrile (5.0 g, 0.01 5 mol) (containing 5.8% amide and 1% desmethylcitalopram impurities) and phosphorous pentoxide ($P_2O_5$) (2.98 g, 0.0 μmol) in xylene (50 ml) was stirred at 140° C. under nitrogen atmosphere for 2 hours, poured into water (100 ml) and NaOH flakes (5.0 g, 0.125 mol) was added to make reaction mixture basic, stirred for 30 minutes separated the xylene layer, dried over sodium sulfate, filtered and concentrated under reduced pressure. The residue checked for HPLC purity and found 0.49% and 0.64% of amide and desmethylcitalopram respectively.

Example 10

4-Fluorophenyl magnesium bromide (prepared from 4-fluro bromobenzene (144 g) and Mg (20.8 g) in 400 ml of THF) was added to the solution of 5-Bromophthalide (100 g) in THF (400 ml) at −5 to −10° C., followed by addition of dimethylaminopropyl magnesium chloride (prepared from dimethylaminopropyl chloride (171 g) and Magnesium (36 g) in 500 ml of THF) at −5 to −10° C. After completion of reaction, it was quenched in saturated ammonium chloride solution at below 5° C., extracted with toluene, after acid-base workup yields product (106 g) in toluene layer. 70% Aqueous ortho phosphoric solution (530 ml) was added to this toluene layer at 15–20° C. and maintained for 4–6 hours. After completion of reaction it was basified with aqueous ammonia, extracted into toluene and concentrated to get the product as a thick oily mass (89 g). This oily mass (50 g) was treated with CuCN (23.6 g) and KI (12.5 g) in Pyridine (50 ml) solvent at 145–160° C. for 10–12 hours. After completion of reaction it was quenched with aqueous ammonia at 50–60° C., extracted with toluene, which after acid-base treatment gave the crude product in toluene layer. This crude product was treated with $POCl_3$ (10 ml) at 70° C. for one hour and then subjected to basification, extraction and distillation to yield citalopram base (30 g) as a thick liquid.

Example 11

35.0 gm of crude citalopram oil obtained after $POCl_3$ treatment was dissolved in 175 ml of IPA and add 29.5 gm 33% HBr in acetic acid at 20–25° C. and maintained for 2 hrs. IPA was concentrated under reduced pressure and 1400 ml of acetone was added, heated to dissolution, charcolised and concentrated to 175 ml volume and cooled to 0–5° C., maintained for 30 min, filtered the material and washed with chilled acetone, dried at 45–50° C. The resultant crude hydrobromide salt dissolved in DM water and pH was adjusted to 9–9.5 with aqueous ammonia and extracted into toluene, concentrated under reduced pressure to get 22 gm crude 1-(3-Dimethylamino)propyl]-1-(4-fluorophenyl)-1,3-dihydro-5-isobenzofuran carbonitrile base.

20.0 g of crude 1-(3-Dimethylamino)propyl]-1-(4-fluorophenyl)-1,3-dihydro-5-isobenzofuran carbonitrile (purity 97.3%) was taken in a mixture of cyclohexane (80 ml) and n-propanol (8 ml) and heated to 60–65° C. to get clear solution and cooled to 5–10° C., the product precipitated was filtered and dried at 40–45° C. under vacuum (HPLC purity 99.54%).

Examples 12 to 18 relate to purification of 1-(3-Dimethylamino)propyl]-1-(4-fluorophenyl)-1,3-dihydro-5-isobenzofuran carbonitrile carried out according to the process of the present invention, from different solvent systems as detailed in Table I.

Comparative Example (iii)

relates to purification of 1-(3-Dimethylamino)propyl]-1-(4-fluorophenyl)-1,3-dihydro-5-isobenzofuran carbonitrile carried out in n-heptane. As is evident from data in Table I, n-heptane purification fails to remove the impurities compared to solvent systems used in the process of the present invention.

Example 19

Treatment of oily citalopram base (40 g) with a mixture of cyclohexane (160 ml) and isopropanol (16 ml) yielded citalopram solid base of 99.52% purity. It was converted to citalopram hydrobromide in isopropanol in a conventional manner. The citalopram hydrobromide obtained was dissolved in acetone, charcolised and concentrated to obtain citalopram hydrobromide (HPLC purity 99.56%).

Example 20

Crude citalopram base oil (10 g) was treated with mixture of cyclohexane (40 ml) and IPA (0.8 ml) at 60–65° C. to get clear solution which after charcolisation and cooling to 3–5° C. gave the solid citalopram base (8.1 g).

The citalopram base was analysed for purity and levels of known impurities by HPLC and the data is given in Table IV.

TABLE IV

| Experiment details | % purity of citalopram before crystallisation | % impurities before crystallisation | | | % impurities present after crystallisation | | | % purity of citalopram after crystallisation |
|---|---|---|---|---|---|---|---|---|
| | | Amide | Desfluoro | Desmethyl | Amide | Desfluoro | Desmethyl | |
| n-heptane | 97.9 | 0.17 | 0.146 | 0.47 | 0.167 | 0.11 | 0.45 | 98.80 |
| Cyclohexane | 97.9 | 0.17 | 0.146 | 0.47 | 0.169 | 0.094 | 0.456 | 99.06 |
| Cyclohexane + 2% IPA | 97.9 | 0.17 | 0.146 | 0.47 | 0.129 | 0.072 | 0.397 | 99.15 |
| Cyclohexane + 2% n-propanol | 97.9 | 0.17 | 0.146 | 0.47 | 0.154 | 0.08 | 0.39 | 99.15 |

Example 21

The citalopram solid base (50 g) was treated with oxalic acid (23.3 g) in acetone (300 ml) to obtain the oxalate salt (54 g). After generating the free base from oxalate salt, it was extracted into toluene and concentrated partially which was treated with 33% HBr in Acetic acid (32.5 ml) in IPA (350 ml) to get crude hydrobromide salt.

TABLE I

Purification of the compound of formula 1 from various solvent systems: % reduction in impurities observed

| Example No. | Solvents | % Solvent Ratio Hydrocarbon solvent: Second solvent | Initial HPLC purity of crude citalopram | Final HPLC purity of citalopram | % reduction of the impurities | | | |
|---|---|---|---|---|---|---|---|---|
| | | | | | Starting 5-bromo compound (2) | Desmethylcitalopram (3) | Amide (4) | Descyanocitalopram (5) |
| Comparative Example (iii) | n-Heptane | 100:0 | 97.3 | 98.79 | 69 | 12 | 0 | 70 |
| Example 12 | n-Heptane: n-Propanol | 90:10 | 97.3 | 98.96 | 69 | 45 | 35 | 72 |
| Example 13 | Cyclohexane: n-Propanol | 90:10 | 97.3 | 99.54 | 75 | 70 | 70 | 100 |
| Example 14 | Cyclohexane: Isopropanol | 90:10 | 97.3 | 99.16 | 75 | 25 | 48 | 100 |
| Example 15 | Cyclohexane: n-Butanol | 90:10 | 97.3 | 98.98 | 69 | 29 | 48 | 88 |
| Example 16 | Cyclohexane: Ethyl acetate | 90:10 | 97.3 | 98.9 | 74 | 17 | 0 | 100 |
| Example 17 | Cyclohexane: Acetone | 90:10 | 97.3 | 98.8 | 66 | 20 | 18 | 88 |
| Example 18 | Cyclohexane: Diethyl ether | 90:10 | 97.3 | 98.8 | 17 | 13 | 9 | 86 |

(2) - starting 5-bromo compound i.e. [1-(3-Dimethylamino)propyl)]-1-(4-fluorophenyl)-1,3-dihydro-5-bromoisobenzofuran;
(3) - desmethylcitalopram impurity; i.e. [1-(3-Methylamino)propyl)]-1-(4-fluorophenyl)-1,3-dihydro-5-isobenzofurancarbonitrile;
(4) - the amide impurity, i.e. [1-(3-Dimethylamino)propyl)]-1-(4-fluorophenyl)-1,3-dihydro-isobenzofuran-5-carboxylic acid amide;
(5) - descyanocitalopram impurity, i.e. [1-(3-Dimethylamino)propyl)]-1-(4-fluorophenyl)-1,3-dihydroisobenzofuran.

TABLE II

HPLC profile of impurities observed for reaction mass of comparative examples (i) and (ii)

| Comparative Example | After 4 hrs | | | | After 10 hrs | | | | After 15 hrs | | | | After 20 hrs | | | |
|---|---|---|---|---|---|---|---|---|---|---|---|---|---|---|---|---|
| | Product | (2) | (3) | (4) | Product | (2) | (3) | (4) | Product | (2) | (3) | (4) | Product | (2) | (3) | (4) |
| (i) | 77.8 | 10.9 | 0.9 | 0.45 | 73.5 | 2.12 | 6.7 | 0.66 | 71.7 | 2.6 | 4.6 | 0.9 | 67.5 | 2.8 | 1.2 | 2.6 |
| (ii) | 71.7 | 18.0 | 0.59 | 1.48 | 77.7 | 6.8 | 1.4 | 1.7 | 74.8 | 3.9 | 2.4 | 3.1 | 56.4 | 0.5 | 6.3 | 7.1 |

Product: 1-[3-(dimethylamino)propyl]-1-(4-fluorophenyl)-1,3-dihydro-5-isobenzofuran carbonitrile;
(2): starting 5-bromo compound i.e. [1-(3-dimethylamino)propyl)]-1-(4-fluorophenyl)-1,3-dihydro-5-bromoisobenzofuran;
(3): desmethylcitalopram impurity; i.e. [1-(3-methylamino)propyl)]-1-(4-fluorophenyl)-1,3-dihydro-5-isobenzofurancarbonitrile
(4): the amide impurity, i.e. [1-(3-dimethylamino)propyl)]-1-(4-fluorophenyl)-1,3-dihydro-isobenzofuran-5-carboxylic acid amide

TABLE III

HPLC Retention time (RT) and area % observed for the high molecular weight impurities (which elute at higher RT) for comparative examples (i) and (ii)

| Comparative Example | | After 4 hrs | | | | After 10 hrs | | | | After 15 hrs | | | | After 20 hrs | | | |
|---|---|---|---|---|---|---|---|---|---|---|---|---|---|---|---|---|---|
| (i) | RT | 26.1 | 28.5 | 30.4 | RT | 26.1 | 28.4 | 30.4 | RT | 26.4 | 28.7 | 30.7 | RT | 26.3 | 28.5 | 30.5 |
| | Area % | — | 0.24 | 2.35 | Area % | 0.07 | 2.07 | 4.44 | Area % | 0.23 | 3.16 | 6.2 | Area % | 0.2 | 6.6 | 11.03 |
| (ii) | RT | | 30.6 | 33.4 | RT | 28.7 | 30.6 | 33.4 | RT | 28.8 | 30.7 | 33.5 | RT | 28.7 | 30.6 | 33.5 |
| | Area % | — | 0.64 | 0.07 | Area % | 0.38 | 3.07 | 0.1 | Area % | 0.95 | 4.56 | 0.1 | Area % | 3.4 | 13.5 | — |

We claim:

1. A process for the preparation of 1-[3-(dimethylamino)propyl]-1-(4-fluorophenyl)-1,3-dihydro-5-isobenzofuran carbonitrile base, a compound of formula 1,

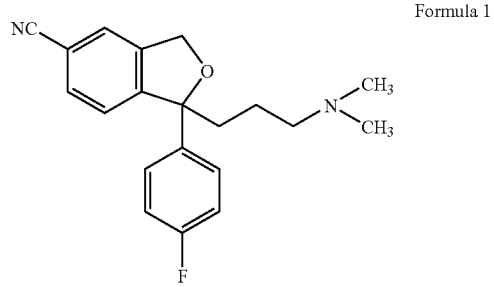

Formula 1 comprising,
  a) reacting a compound of formula 2, wherein R is Cl or Br,

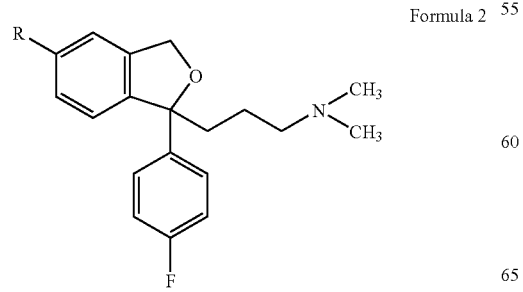

Formula 2 with a cyanide source in presence of an iodide and a suitable solvent selected from the group consisting of amides, amines and polyethers, to obtain the compound of formula 1,
  b) treating the resultant crude compound of formula 1 obtained in step a) containing, a compound of formula 3, and, a compound of formula 4,

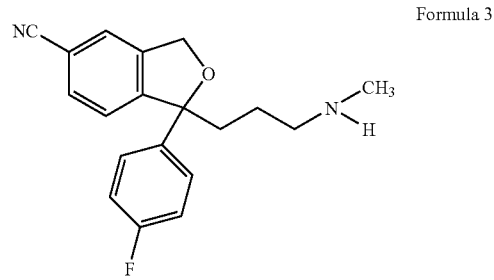

Formula 3

Formula 4 with a cyanide reversal agent, wherein the cyanide reversal agent is selected from phosphorous oxyhalides and phosphorous oxides; and isolating the base of compound of formula 1 from the reaction mixture, wherein the compound of formula 1 obtained after isolation has substantially low levels of impurities of formula 3 and formula 4, and optionally converting the compound of formula 1 obtained after isolation, to a pharmaceutically acceptable salt thereof, followed by the conversion of the salt of compound of formula 1 to the base of compound of formula 1, c) further purifying the resultant compound of formula 1 obtained in step 'b', from a solvent system, wherein the solvent system comprises a first solvent which is a hydrocarbon solvent and a second solvent, wherein the second solvent is selected from a group consisting of alcohol, ester, ether, ketone or mixture thereof.

2. A process for the preparation of 1-[3-(dimethylamino) propyl]-1-(4-fluorophenyl)-1,3-dihydro-5-isobenzofuran carbonitrile base, a compound of formula 1,

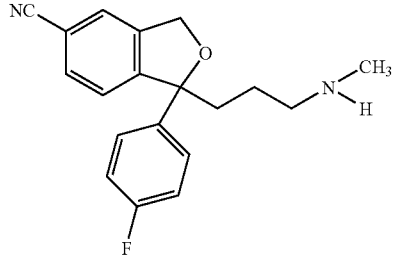

Formula 1 comprising reacting a compound of formula 2, wherein R is Cl or Br,

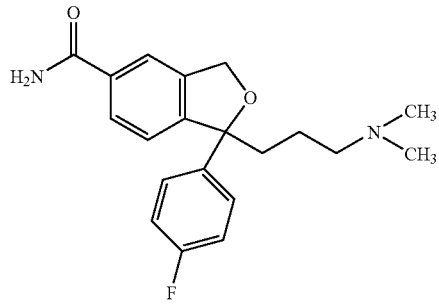

Formula 2 with a cyanide source in presence of an iodide and a suitable solvent selected from the group consisting of amides, amines and polyethers.

3. A process for preparation of 1-[3-(dimethylamino) propyl]-1-(4-fluorophenyl)-1,3-dihydro-5-isobenzofuran carbonitrile base, a compound of formula 1,

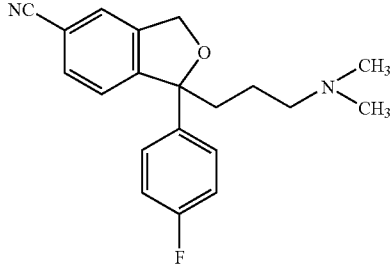

FORMULA 1 with substantially low levels of impurities, comprising treating the crude compound of formula 1, containing, a compound of formula 3, a compound of formula 4,

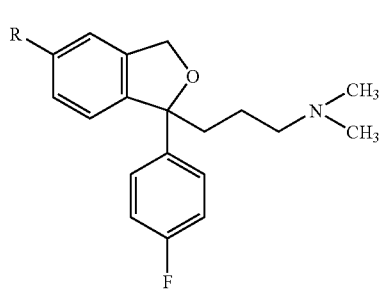

Formula 3

Formula 4 with a cyanide reversal agent, wherein the cyanide reversal agent is selected from phosphorous oxyhalides and phosphorous oxides; and isolating the base of compound of formula 1 from the reaction mixture, and optionally converting the compound of formula 1 obtained after isolation, to a pharmaceutically acceptable salt thereof, followed by the conversion of the salt of compound of formula 1 to the base of compound of formula 1.

4. The process as claimed in claim 2 wherein the cyanide source is selected from the group consisting of KCN, NaCN, CuCN and $[R_1R_2R_3R_4N]CN$, wherein $R_1$, $R_2$, $R_3$ and $R_4$ are the same or different groups selected from hydrogen and straight chain or branched alkyl.

5. A process as claimed in claim 2 wherein the iodide is selected from the group of stable metal iodides, alkali and alkaline earth metal iodides.

6. The process as claimed in claim 2 wherein the cyanide source is CuCN, the iodide is potassium iodide and the group R in compound of formula 2 is Br.

7. The process as claimed in claim 2 wherein the reaction of compound of formula 2 with a cyanide source is carried out in an amine solvent wherein the amine solvent is selected from pyridine and lutidine.

8. The process as claimed in claim 2 wherein the reaction of compound of formula 2 with a cyanide source is carried out at a temperature between the range of about 100° C. to about 200° C. for about 10 to about 30 hours.

9. The process as claimed in claim 8 wherein the reaction of compound of formula 2 with a cyanide source is carried out at a temperature between the range of about 130° C. to about 150° C. for about 20 to about 28 hours.

10. The process as claimed in claim 3 wherein the cyanide reversal agent is phosphorous oxychloride.

11. The process as claimed in claim 3 wherein the cyanide reversal agent is phosphorous pentoxide.

12. The process as claimed in claim 3, wherein after treatment of compound of formula 1 with a cyanide reversal agent, the resultant compound of formula 1 contains less than about 1% desmethylcitalopram, a compound of formula 3 and less than about 1% amide, a compound of formula 4, after isolation from the reaction mixture.

13. The process as claimed in claim 3, wherein after treatment of compound of formula 1 with a cyanide reversal agent, the resultant compound of formula 1 contains less than about 0.5% desmethylcitalopram, a compound of formula 3 and less than about 0.5% of the amide, a compound of formula 4, after isolation from the reaction mixture, characterized in that the cyanide reversal agent is phosphorous oxychloride.

14. The process as claimed in claim 3 wherein the ratio of the cyanide reversal agent to the crude compound of formula 1 containing the impurities of formula 3 and formula 4, is in the range from about 0.1 to about 5.

15. The process as claimed in claim 3 wherein the ratio of the cyanide reversal agent to the crude compound of formula 1 containing the impurities of formula 3 and formula 4, is in the range from about 0.1 to about 2.

16. The process as claimed in claim 3 wherein the ratio of the cyanide reversal agent to the crude compound of formula 1 containing the impurities of formula 3 and formula 4, is in the range from about 0.2 to about 2.

17. The process as claimed in claim 3 wherein the reaction of the crude compound of formula 1 containing the impurities of formula 3 and formula 4, with a cyanide reversal agent is carried out in an aprotic organic solvent.

18. The process as claimed in claim 17 wherein the aprotic organic solvent is selected from the group consisting of ethers, halogenated solvents, aliphatic hydrocarbons, aromatic hydrocarbons, esters, nitriles and nitro compounds.

19. The process as claimed in claim 18 wherein the aromatic hydrocarbon solvent is selected from toluene and xylenes.

20. The process as claimed in claim 3 wherein the reaction of the crude compound of formula 1 containing the impurities of formula 3 and formula 4, with a cyanide reversal agent is carried out at a temperature between the range of ambient to about 200° C. for about 1 to about 20 hours.

21. The process as claimed in claim 20 wherein the reaction is carried out at a temperature between the range of about 50° C. to about 150° C. for about 1 to about 5 hours.

22. The process as claimed in claim 1 wherein,
   i. a compound of formula 2 wherein R is Br, is reacted with CuCN in presence of potassium iodide, in pyridine solvent to obtain the compound of formula 1,
   ii. the resultant crude compound of formula 1 obtained in step a) is treated with $POCl_3$ and the compound of formula 1 is isolated from the reaction mixture, and optionally converted to a pharmaceutically acceptable salt thereof, followed by the conversion of the salt of compound of formula 1 to the base of compound of formula 1,
   iii. the resultant compound of formula 1 obtained in step b) is purified from a solvent system comprising cyclohexane as the first solvent and n-propanol or isopropanol as the second solvent.

23. The process as claimed in claim 1, wherein the compound of formula 1 obtained is further converted to its hydrobromide salt.

24. The process as claimed in claim 22, wherein the compound of formula 1 obtained is further converted to its hydrobromide salt.

25. The process as claimed in claim 1, wherein the compound of formula 1 obtained is further converted to citalopram hydrobromide having a HPLC purity greater than 99.5%.

26. The process as claimed in claim 22, wherein the compound of formula 1 obtained is further converted to citalopram hydrobromide having a HPLC purity greater than 99.5%.

* * * * *